(12) United States Patent
Vacher et al.

(10) Patent No.: US 10,626,370 B2
(45) Date of Patent: *Apr. 21, 2020

(54) PROCESS FOR PREPARING A CELL SUSPENSION

(71) Applicant: LABORATOIRES GENEVRIER, Antibes (FR)

(72) Inventors: Dominique Vacher, Mougins (FR); Jean-Noel Gouze, Vallauris (FR)

(73) Assignee: LABORATOIRES GENEVRIER, Antibes (FR)

( * ) Notice: Subject to any disclaimer, the term of this patent is extended or adjusted under 35 U.S.C. 154(b) by 37 days.

This patent is subject to a terminal disclaimer.

(21) Appl. No.: 15/933,321

(22) Filed: Mar. 22, 2018

(65) Prior Publication Data

US 2018/0298334 A1    Oct. 18, 2018

Related U.S. Application Data

(63) Continuation of application No. 14/405,965, filed as application No. PCT/IB2013/053015 on Apr. 16, 2013, now Pat. No. 9,926,530.

(30) Foreign Application Priority Data

Jun. 7, 2012 (FR) ........................... 12 55333

(51) Int. Cl.
| | | |
|---|---|---|
| *C12M 1/38* | (2006.01) | |
| *C12N 5/071* | (2010.01) | |
| *C12M 1/34* | (2006.01) | |
| *C12M 1/00* | (2006.01) | |
| *B01L 7/00* | (2006.01) | |
| *C09K 5/06* | (2006.01) | |
| *C12M 1/22* | (2006.01) | |
| *B01L 9/00* | (2006.01) | |

(52) U.S. Cl.
CPC ............. *C12N 5/0626* (2013.01); *B01L 7/00* (2013.01); *C09K 5/063* (2013.01); *C12M 23/10* (2013.01); *C12M 41/12* (2013.01); *C12M 45/09* (2013.01); *C12M 45/20* (2013.01); *B01L 9/52* (2013.01); *B01L 2300/1855* (2013.01); *B01L 2300/1877* (2013.01); *C12N 2509/00* (2013.01); *C12N 2523/00* (2013.01); *Y02E 60/145* (2013.01)

(58) Field of Classification Search
None
See application file for complete search history.

(56) References Cited

U.S. PATENT DOCUMENTS

| | | | |
|---|---|---|---|
| 4,451,383 A | 5/1984 | Arrhenius | |
| 6,136,217 A | 10/2000 | Haget | |
| 6,723,115 B1 | 4/2004 | Daly | |
| 8,216,183 B2 | 7/2012 | Blakeley | |
| 9,078,741 B2 | 7/2015 | Wood | |
| 9,926,530 B2 * | 3/2018 | Vacher | C12M 41/12 |
| 2002/0106353 A1 | 8/2002 | Wood et al. | |
| 2004/0161845 A1 | 8/2004 | Poo et al. | |
| 2004/0261783 A1 | 12/2004 | Madan et al. | |
| 2009/0004732 A1 | 1/2009 | LaBarre et al. | |
| 2010/0190250 A1 * | 7/2010 | Hu | C12N 5/0696 |
| | | | 435/377 |
| 2012/0193347 A1 | 8/2012 | Schwartz | |
| 2018/0171290 A1 * | 6/2018 | Bhasin | C12N 5/0607 |

FOREIGN PATENT DOCUMENTS

| | | |
|---|---|---|
| FR | 2678943 A1 | 1/1993 |
| FR | 2967756 A1 | 5/2012 |

OTHER PUBLICATIONS

Mulekaret al., "Treatmentof vitiligo lesions by ReCell vs. conventionalmelanocyte-keratinocytetransplantation:a pilot • study," British Journal of Dermatology, 158: 45-49 (2008).
International Search Report issued in corresponding International Patent Application No. PCT/IB2013/053015 dated Jul. 19, 2013.
Written Opinion issued in corresponding International Patent Application No. PCT/IB2013/053015 dated Jul. 19, 2013.
Liu, C., et al., "A self-heating cartridge for molecular diagnostics," Lab Chip, 2011, 11, 2686.

* cited by examiner

*Primary Examiner* — Ralph J Gitomer
(74) *Attorney, Agent, or Firm* — Arrigo, Lee, Guttman & Mouta-Bellum LLP

(57) ABSTRACT

Process for carrying out an in vitro biochemical reaction for preparing a cell suspension suitable for application to the skin of a patient.

14 Claims, 4 Drawing Sheets

PROCESS FOR PREPARING A CELL SUSPENSION

Figure 1:
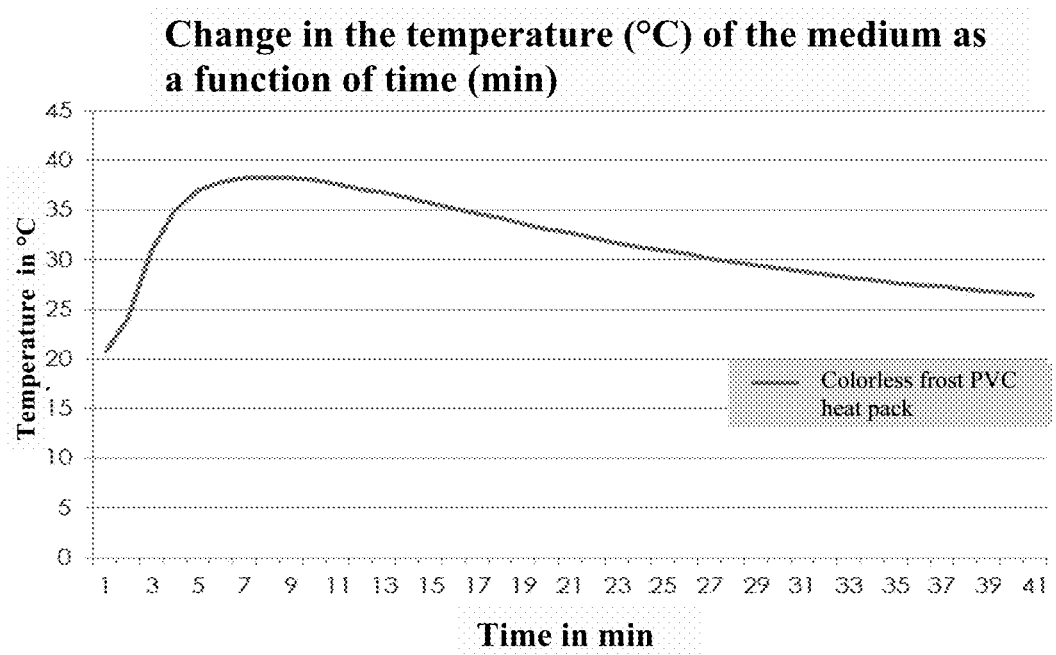

The present invention relates to the field of molecular and cell biology kits, and also to that of kits for carrying out a chemical reaction requiring a moderate provision of heat. The subject of the present invention is in particular kits comprising a simple and inexpensive autonomous heating means for treating biopsies.

For several years, the grafting of cells, in particular of autologous cells, has been essential as an effective and safe means for promoting the regeneration of diseased or damaged tissues. Certain therapeutic protocols require the proliferation and/or the modification of the cells ex vivo before reimplantation. Other protocols essentially provide for the sampling of cells from a healthy part of the tissue concerned and the virtually immediate reimplantation thereof at the lesion to be treated. This is in particular the case with protocols for the treatment of skin diseases or lesions such as certain burns (the extent of which does not require cell expansion), post-traumatic and post-operative hypochromia, achromatic dermatosis, scars, etc. In these protocols, the treatment of the samples essentially amounts to a more or less thorough dissociation of the cells, followed, where appropriate, by the separation of various cell types in order to select the cells appropriate for the intended application (melanocytes for achromatic dermatosis, for example) and by filtration in order to remove the aggregates. The cell dissociation is usually carried out by incubating the sample in a trypsin solution. The optimal temperature for trypsin activity is 37° C. At this temperature, and depending on the concentration of enzyme and the desired degree of dissociation, the incubation times described in the literature are between 50 minutes and 3 hours (Guerra et al., 2003; Mulekar, 2003; van Geel et al., 2004). At a lower temperature, the enzyme is less active, and it is necessary to prolong the incubation time by several hours, thereby making it impossible to carry out all the steps of the protocol in the same day (Gauthier and Surleve-Bazeille, 1992). For this reason, these protocols are currently carried out at least partially in structures which have technical platforms comprising an incubator, which is not often the case with dermatology practices.

In order to enable practitioners not equipped with an incubator to treat patients suffering from vitiligo, the company Clinical Cell Culture provides a kit (ReCell®) comprising the consumables required for carrying out all the steps, from the sampling to the reimplantation of the cells, and also an electronic heating unit equipped with batteries. This device has two major drawbacks, which are its very high price and its ecological impact.

The present invention provides an advantageous alternative to the prior art solutions, in particular to the ReCell® kit, since it is based on the use of warmers for heating and maintaining an enzymatic solution at a suitable temperature, during the period of time required for the action of the enzyme. The term "warmer" denotes herein the small objects capable of emitting heat, also called "magical heat packs" or "autonomous heat packs", the operation of which is based on exothermic physical or chemical processes. They are commonly used to heat the hands or feet exposed to cold. In the rest of the text, the terms "warmer" and "heat pack" are used without distinction. By way of example of a warmer based on a physical process, mention may be made of the reusable warmers consisting of a pouch containing a supercooled sodium acetate-saturated aqueous solution. By bending a metal disk inside the liquid, crystals of solidified acetate are generated, which trigger crystallization, and the solution becomes solid. Since this phase transition takes place at the melting point (54° for a 20% solution, for example), there is heating of the pouch and then cooling to ambient temperature once the solidification is complete. When the pouch is cooled, it is possible to return the sodium acetate (which has become solid) to the liquid state, by placing the pouch in very hot water. Chemical warmers also exist, the constituent of which is activated by oxidation on contact with air. They are effective for longer (from 8 to 60 hours compared with approximately 1 hour for supercooled sodium acetate-based warmers) but can only be used once.

The inventors have shown (examples 1 and 3 below) that a solution placed in a container, typically a Petri dish, placed on a warmer, reaches, in a few minutes, an optimum temperature for the activity of numerous enzymes, such as trypsin, and stays at said temperature for at least 15 to 20 minutes.

The invention therefore relates, firstly, to a process for carrying out a biological, biochemical or chemical reaction requiring an incubation at a temperature between 30 and 40° C., characterized in that it comprises a step of activating a warmer, the operation of which is based on an exothermic physical or chemical process, and a step of bringing said warmer into contact with a container containing the reagents involved in said reaction. This process is particularly advantageous in the context of a biological, medical or diagnostic application.

In one particular implementation of this process, the step of bringing the warmer into contact with the container is carried out by placing the warmer and at least the lower part of the container in a cavity of a support provided for this purpose. Such a support makes it possible, firstly, to properly wedge the container on the warmer, thus limiting the risks of tipping. In addition, the use of an insulating support, having a low thermal conductivity, makes it possible to limit heat losses from the warmer and to promote transfer of the heat from the warmer to the solution to be heated. In one preferred implementation, the depth of the cavity makes it possible to place therein the warmer and only the lower part of the container. In this way, the container is properly wedged on the warmer, there is no risk of it sliding, and it remains easy for the operator to grasp.

In the above processes, the use of a warmer and, where appropriate, an insulating support, makes it possible to maintain the temperature of a biological, biochemical or chemical solution between 30 and 40° C. for the required period of time (from a few minutes to a few tens of minutes, for example 5, 10, 15, 18, 20 minutes or more). This use of the warmer, which is a simple, inexpensive object generally intended for outdoor leisure activities (skiing, mountaineering, etc.), for carrying out a biological (molecular or cell biology) or chemical process as a replacement for a sophisticated piece of laboratory equipment, is as advantageous as it is surprising, since it enables considerable savings without impairing the quality of the results obtained.

In the aforementioned, the term "biological reaction" is applied to any reaction involving elements derived from a living being, for instance living cells (animal cells originating from a biopsy, plant cells, yeasts or bacteria), viruses, organelles, enzymes, metabolic products, etc. A "biochemical reaction" uses substances involved in chemical reactions of living matter (enzymes, sugars, lipids, etc.).

According to one particular embodiment of the process of the invention, the container contains an enzymatic solution and the contact between the warmer and the container is maintained for at least 10 minutes. According to one particular embodiment, the warmer is used in the context of a cell biology process, and the enzymatic solution contains cells originating from a biopsy, for example a sample of tissue to be dissociated. In this case, the enzymatic solution contains, for example, trypsin.

For reactions requiring an incubation of less than one hour, the warmer preferably consists of a hermetic plastic pouch containing a sodium acetate-saturated aqueous solution. However, the invention can also be used with a chemical warmer, enabling a longer incubation.

According to one particular embodiment of the process of the invention, the warmer used, of pouch type containing sodium acetate, is a disk of which the thickness is between 3 and 7 mm, preferably 4 to 6 mm, and the diameter is between 7 and 11 cm, preferably 8 to 10 cm, and the solution containing the reagents involved in the reaction has a volume between 3 and 10 ml and is contained in a Petri dish having a diameter between 7 and 11 cm, preferably between 8 and 10 cm, or a compartment of said dish. The term "Petri dish" is intended to mean herein a shallow transparent cylindrical dish, made of glass or plastic, with a lid. In certain particular implementations of the invention, the Petri dish is compartmentalized, for example by means of a small wall along one diameter. When a support is used in the context of this particular embodiment, the cavity intended to receive the warmer is also circular, with a diameter slightly larger than that of the warmer (between 7 and 11.5 cm), and has a depth of between 5 and 20 mm.

The present invention also relates to a process for dissociating cells derived from a freshly taken tissue sample, comprising the following steps:
(i) initiating the crystallization in a warmer consisting of a hermetic plastic pouch containing a sodium acetate-saturated aqueous solution; optionally, placing said warmer in a cavity provided for this purpose in a support, preferably an insulating support;
(ii) placing on said warmer a container containing a solution of trypsin having a concentration between 0.2% and 1%;
(iii) placing the tissue sample in said solution and leaving to incubate for at least 10 minutes, preferably 15 to 20 minutes;
(iv) rinsing the tissue sample.

Of course, during the implementation of this process, care will be taken to ensure that the geometries of the warmer, of the container and, where appropriate, of the cavity of the insulating support are such that there is a large surface area of exchange between the warmer and the container. According to one particular embodiment, the warmer has a disk shape and the container is a Petri dish, as mentioned above. In this case, the diameters of these two elements are preferably identical or virtually identical; if a support is used, the cavity of the support intended to receive at least the warmer is also circular, with a diameter slightly larger than the diameter of the warmer and of the container.

In the process above, step (iv) can, where appropriate, be preceded or followed by a step of inhibiting the trypsin, by adding an inhibitor. However, according to one preferred embodiment of the process according to the invention, no trypsin inhibitor is added, the rinsing of the tissue sample being sufficient to stop the action of the trypsin. This makes it possible in particular to limit the number of substances that will be applied to the patient with the cells.

The present invention also relates to a process for preparing a cell suspension suitable for application to the skin of a patient, comprising the following steps:

(i) carrying out the dissociation process described above on a skin tissue sample comprising cells appropriate for a graft to a patient;
(ii) harvesting the appropriate cells originating from the skin sample and suspending them in a solution; where appropriate, this step requires an intermediate step of separating and/or sorting certain cells from the sample; and
(iii) filtering the solution obtained in step (ii) on a cell sieve.

According to one particular embodiment, the process above comprises an additional step of adding hyaluronic acid to the cell suspension obtained in step (iii). This step makes it possible to obtain a viscous mixture which is easily applied in the wound bed. In addition, the hyaluronic acid promotes cell viability.

One particular application of the processes above is the treatment of vitiligo; in this application, the cells recovered in step (ii) comprise at least melanocytes.

The present invention also relates to a kit for biological application (cell biology kit and/or molecular biology kit), characterized in that it comprises a warmer, the operation of which is based on an exothermic physical or chemical process.

According to one preferred embodiment of the kits according to the present invention, the warmer consists of a hermetic plastic pouch containing a supercooled sodium acetate-saturated aqueous solution.

According to one preferred embodiment of the kit of the present invention, the kit also contains a support which comprises a cavity intended to receive the warmer. This support comprises, for example, a plate of thermally insulating material having a thickness between 5 and 35 mm, in which the cavity intended to receive the warmer has a depth between 5 and 25 mm. The support can also consist of a thinner plate (for example 1 mm thick), bent or assembled to form a hollow support. Preferably, the material used for the support has a thermal conductivity $\lambda$ less than or equal to 0.4 $W \cdot m^{-1} \cdot K^{-1}$ at 20° C. More preferably, its thermal conductivity is less than 0.15 $W \cdot m^{-1} \cdot K^{-1}$, or even less than 0.08 $W \cdot m^{-1} \cdot K^{-1}$ or even less than or equal to 0.04 $W \cdot m^{-1} \cdot K^{-1}$. By way of nonlimiting examples of usable materials, mention may be made of wood ($\lambda$ of plywood=0.11 $W \cdot m^{-1} \cdot K^{-1}$), cardboard ($\lambda$=0.07 $W \cdot m^{-1} \cdot K^{-1}$), cork ($\lambda$=0.04 $W \cdot m^{-1} \cdot K^{-1}$), PVC ($\lambda$=0.2 $W \cdot m^{-1} \cdot K^{-1}$), polypropylene ($\lambda$=0.1 to 0.22 $W \cdot m^{-1} \cdot K^{-1}$), rigid polyurethane foam ($\lambda$=0.025) and expanded polystyrene ($\lambda$=0.036). According to the applications envisioned for the kit, the insulating nature of the support is more or less important. For example, for a kit intended to prepare, in a dermatology practice, a cell suspension by means of a process as described above, the insulating nature of the support is secondary, since the premises in which the kit will be used are generally at at least 18° C., and the incubation time of the cell sample with the trypsin is not very long. On the other hand, certain applications may impose extreme heat conditions and/or require a longer incubation time at a temperature between 30 and 40° c. In this case, it is important to use an insulating support, which can, where appropriate, be supplemented with a lid for keeping the heat in the container for longer. By way of nonlimiting examples of such applications requiring an incubation of more than one hour between 30 and 40° C., mention may be made of the enzymatic digestion of cartilage, in order to isolate chondrocytes; the digestion of a testicular biopsy, in order to isolate germ cells; the obtaining of islets of Langerhans from a pancreatic biopsy; the digestion of dermis, in order to isolate fibroblasts; and the digestion of a gingival biopsy, in order to isolate gingival fibroblasts.

The kits of the invention can also comprise a container, the base of which has the same geometry as that of the warmer and, where appropriate, of the cavity of the support, in order to allow efficient heat exchanges. For example, the warmer can be a disk of which the thickness is between 3 and 7 mm, preferably 4 to 6 mm, and the diameter is between 7 and 11 cm, preferably from 8 to 10 cm; in this case, the container is preferably a Petri dish having a diameter approximately equal to that of the warmer and, if a support is present, the cavity intended to receive the warmer is also circular, with a diameter slightly larger than that of the warmer.

A kit according to the present invention can also contain an enzyme, for example trypsin. Such a kit is, for example, designed for the treatment of a biopsy, and comprises in particular the means required for dissociating the cells of said biopsy. According to one particular embodiment, this kit comprises a Petri dish divided into compartments, the diameter of which is identical or very close to that of the warmer, a cell sieve, and trypsin (in lyophilized form or in solution).

The following examples and figures illustrate the invention without, however, limiting its scope.

FIGURE LEGENDS

FIG. 1: Change in the temperature of a buffer solution in a Petri dish 9 cm in diameter, placed on a sodium acetate warmer, having the shape of a disk with a diameter approximately equal to that of the Petri dish, over a period of 40 minutes, in a room at 20° C.

Figure 2:
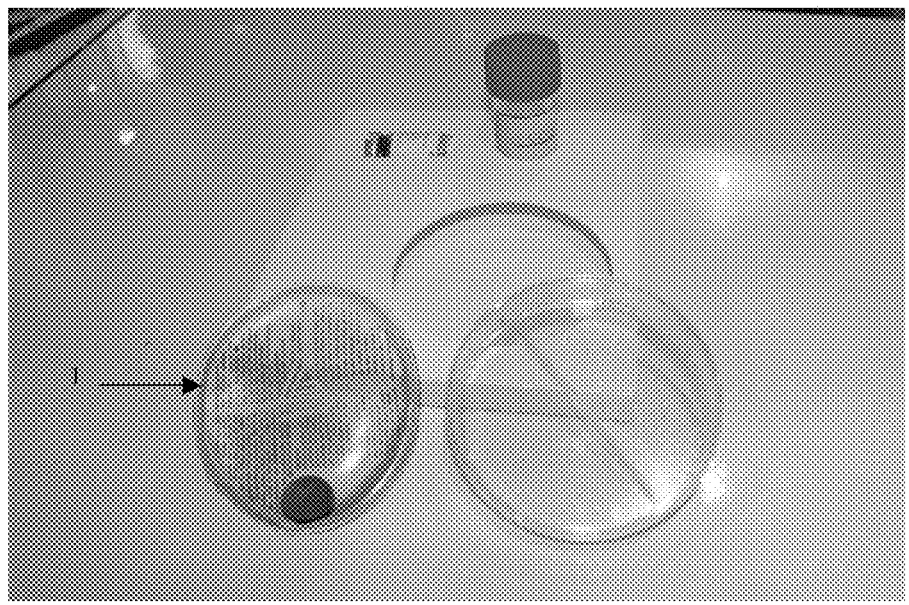
Figure 2:
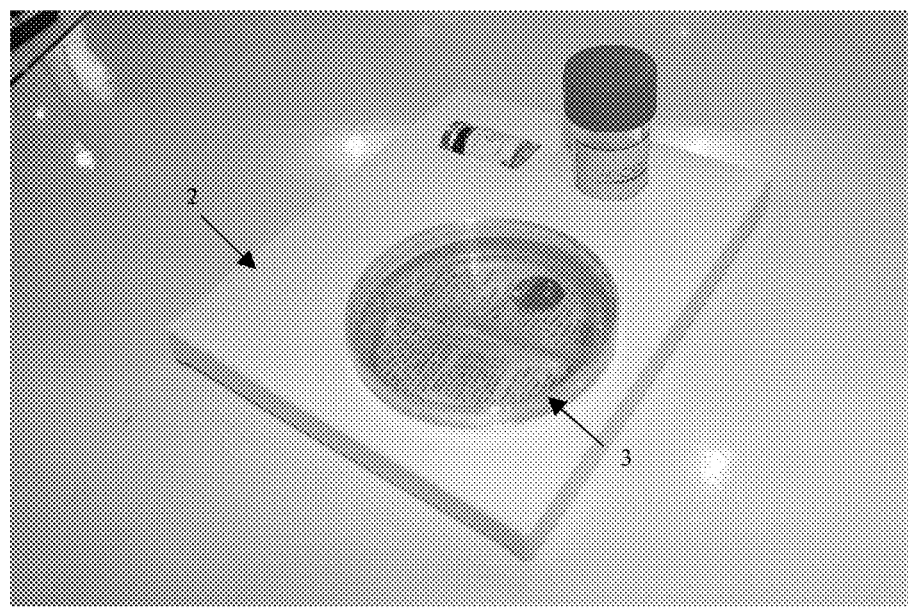

FIG. 2: Photos of the device comprising a support and a heat pack (warmer). 1: heat pack; 2: support; 3: compartmentalized dish placed on the heat pack.

Figure 3:
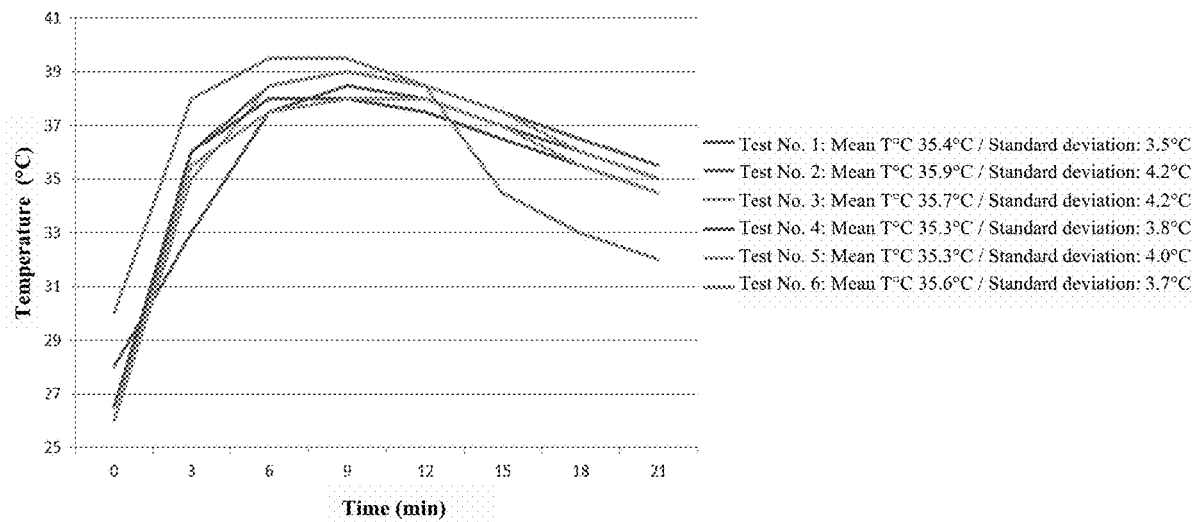

FIG. 3: Change in the temperature as a function of time, without support.

Figure 4:
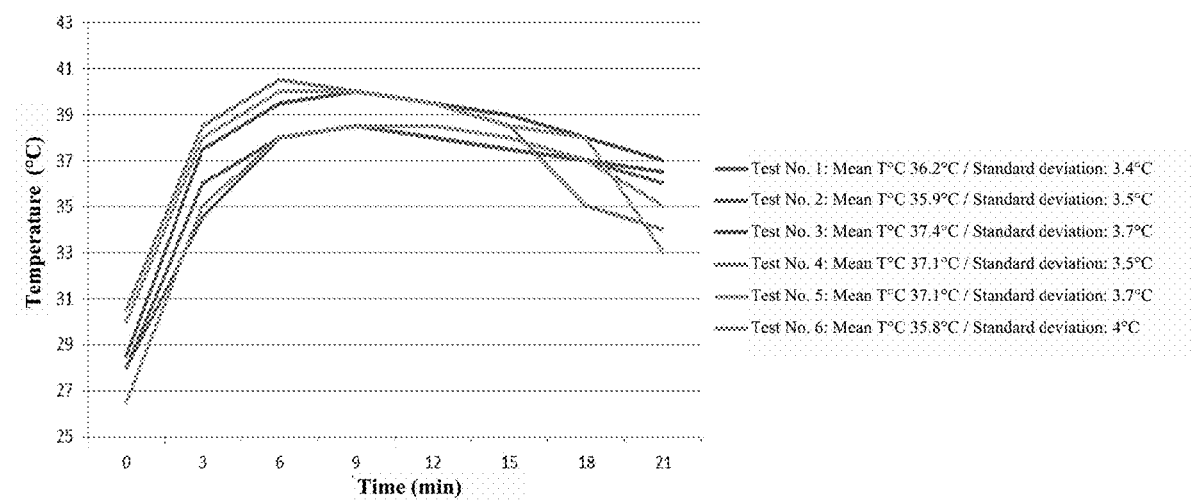

FIG. 4: Change in the temperature as a function of time, with the support V2.

Figure 5:
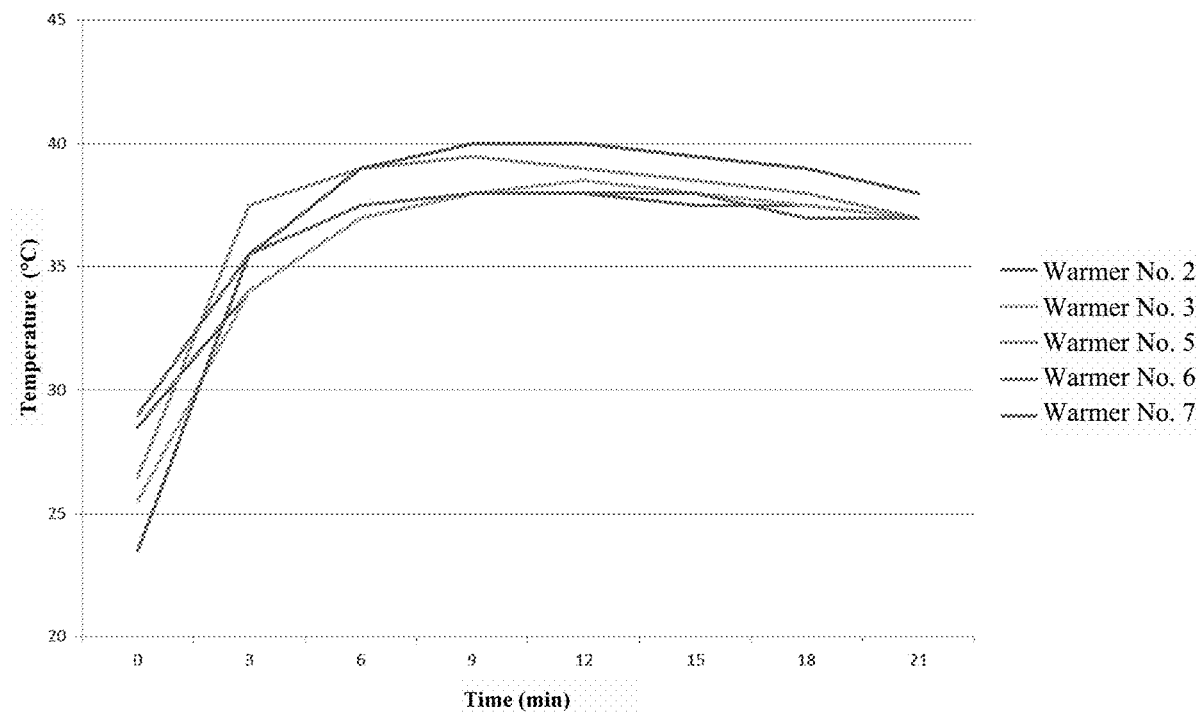

FIG. 5: Change in the temperature as a function of time, with the support V3.

Figure 6:
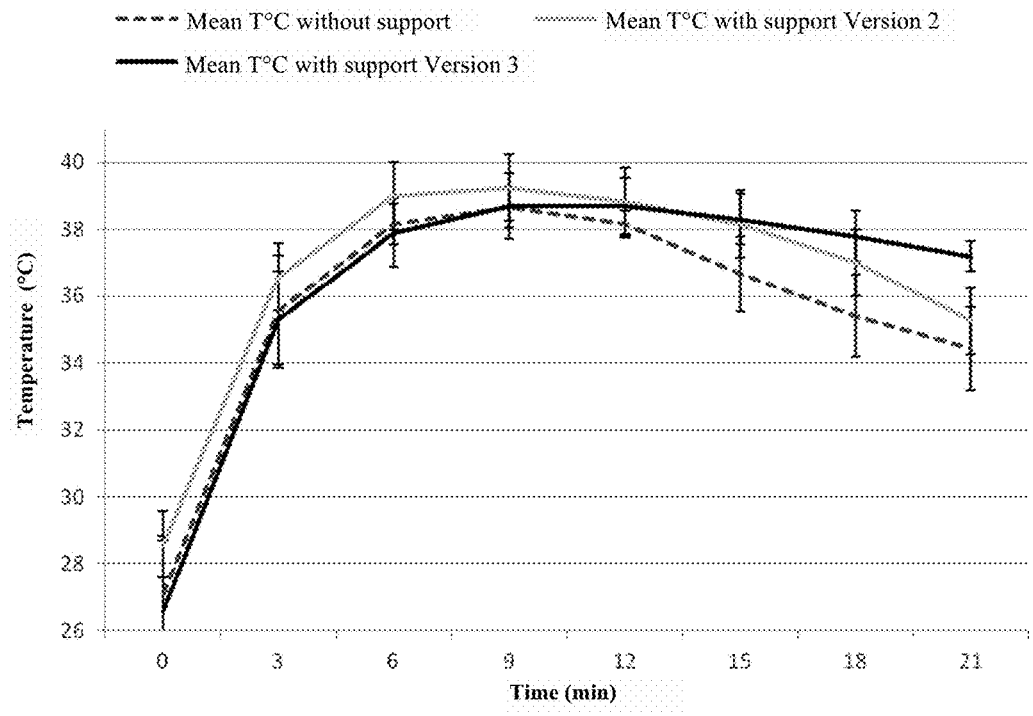

FIG. 6: Change in the temperature as a function of time (comparison of the means without support and with supports V2 or V3).

EXAMPLES

Example 1: Temperature of the Medium in a Petri Dish Placed on a Warmer

The temperature of a (buffer) solution in a Petri dish 9 cm in diameter, placed on a sodium acetate warmer, having the shape of a disk with a diameter approximately equal to that of the Petri dish and a thickness between 4 and 6 mm, was measured.

The results (FIG. 1) show quite a rapid increase in temperature, since the temperature reaches 30° C. in a few minutes. The temperature then remains between 30 and 40° C. for a little more than 20 minutes.

These results showed good reproducibility.

Example 2: Application to Dermo-Epidermal Separation, in the Context of the Treatment of Vitiligo by Autologous Graft of Melanocytes Using a thin skin biopsy (0.2 mm-0.3 mm), the bed of a wound is seeded with autologous cells.

The cell suspension obtained after disaggregation of the graft consists of a mixed population, mainly basal keratinocyte cells, but also Langerhans cells, melanocytes and fibroblasts.

Materials Used

A warmer as described in example 1 and a disposable kit composed of ancillary elements and instruments: enzymatic and application solutions, sterile instruments, including a two-compartment Petri dish.

Protocol

A sterile surgical field is prepared.

Upon reception, the kit is stored at +4° C. until use. The kit is placed at ambient temperature 10 min before use.

Preparation and Heating of the Enzymatic Solution

Using a 5 ml syringe and a needle, take 5 ml of PBS solution and inject them into the bottle of lyophilized trypsin. Homogenize thoroughly before taking up the regenerated solution and in one compartment of the two-compartment Petri dish.

Activate the heat pack instantaneously by crumpling the metal plate; the crystal solidifies instantaneously.

Place the two-compartment Petri dish on the activated heat pack and wait 5 min.

Taking a Skin Sample

The zone from which a sample is to be taken is delimited with a surgical felt tip pen, disinfected with 0.5% chlorhexidine in alcoholic solution, and anesthetized with 2% xylocaine. A thin strip of skin which has a minimum surface area of 4 $cm^2$ and a thickness of 0.2-0.3 mm is taken with a dermatome.

Carrying Out the Dermo-Epidermal Separation (DES)

Using sterile forceps (not provided), transfer the biopsy into the Petri dish compartment containing the trypsin in solution at 0.4%.

Incubate for 15 minutes.

Rinsing of the biopsy:

With the same 5 ml syringe and a needle, take 5 ml of PBS solution and place in the second compartment of the Petri dish.

At the end of the incubation, using sterile forceps, transfer the biopsy into the second compartment, for rapid rinsing with PBS.

Using sterile forceps, place the biopsy inside the lid of the Petri dish, taking care to keep the direction of the dermo-epidermal junction facing upward.

Using the forceps, separate the two fragments.

Preparation of the Cell Suspension

Using the second 5 ml syringe and a needle, take 1.5 ml of PBS and place them on the biopsy fragments, scrape the cells from the junction surfaces with a scalpel (not provided) and coarsely cut up the epidermal part so as to produce a mixture of cells.

Set aside and immobilize the dermal part.

Tilt the Petri dish so as to suction up the entire volume using the 5 ml syringe, draw the cells up into the syringe and suction several times so as to create a cell suspension.

Cell Filtration

Transfer the cell suspension into the sieve that will have been placed on the pot with the red cap.

Preparation of the Cell Suspension in Hyaluronic Acid

Remove the sieve.

Place the hyaluronic acid contained in the syringe (i.e. 1.5 ml) in the pot with the red cap containing the filtered cell suspension.

Using the syringe, mix the hyaluronic acid and the cell suspension so as to obtain a viscous but homogeneous suspension.

The suspension thus prepared is ready to be deposited by syringe on the wound bed.

Results

The protocol above was carried out several times, on three different skin samples, using two trypsin concentrations (0.4% and 0.8%).

The results obtained are summarized in table 1 below.

TABLE 1

| Identification | Trypsin concentration | Number of cells isolated × $10^6/cm^2$ | Cell viability (%) | Cloning efficiency test | Presence of melanocytes by flow cytometry |
| --- | --- | --- | --- | --- | --- |
| Biopsy 1 | 0.4% | 1.2 | 95.0% | 3.4% | >0.1% |
|  | 0.8% | 1.2 | 97.0% | 3.4% | >0.1% |
| Biopsy 2 | 0.4% | 3.4 | 98.0% | 3.3% | >0.1% |
|  | 0.8% | 2.3 | 97.0% | 3.8% | >0.1% |
| Biopsy 3 | 0.4% | 4.2 | 97.4% | 4.6% | >0.1% |
|  | 0.8% | 3.9 | 99.4% | 4.5% | >0.1% |

Trypsin Concentration

The process for obtaining the active substance was adapted from the technique described by van Geel et al. (van Geel et al., 2004).

The concentration of the trypsin solution was optimized (0.4% or 0.8% trypsin instead of 0.25% trypsin/0.08% EDTA). Unlike the technique described by van Geel et al., the inhibition of the trypsin was not carried out by adding inhibitor of fetal calf serum type, but by rinsing with PBS, in order to reduce the number of products of biological origin used for the production of the product. The cell viability after this mode of trypsin inhibition was validated.

Cell Viability

The cell viability was determined according to a conventional cell culture technique: the trypan blue exclusion test. A volume-for-volume dilution of trypan blue and of the cell suspension was carried out in a hemolysis tube. After a contact time of 1 to 2 minutes, the mixture was deposited with a micropipette between slide and coverslip on a counting cell. The dead cells, stained blue, and the live cells, unstained, were counted using a phase contrast optical microscope.

The cell viability was very satisfactory after isolation of the epidermal cells (greater than 90%).

The behavior of the cells after being put back in culture and the cloning efficiency were uniform from one biopsy to the other and showed that the cell suspension contained cells capable of proliferating after trypsinization.

Number of Cells Isolated/Cm of Biopsy

Calculation carried out on the basis of the results of the test described above.

The number of cells isolated was variable from one individual to another depending on the size of the biopsies treated, but the cell yield/$cm^2$ was relatively constant. The cell density of the final suspension therefore depends greatly on the size of the biopsy treated.

Cloning Efficiency Test (CFE)

The cloning efficiency percentage makes it possible to evaluate the amount of cells capable of adhering and of forming colonies. A known amount of epidermal cells was seeded into 3 T25 $cm^2$ flasks. Around the 14th day of culture, when the clones were sufficiently large but not joining up, the flasks were stained with a solution of crystal violet (10% formaldehyde/0.5% crystal violet, qs distilled water). The cloning efficiency was calculated by producing the ratio of the mean of the total number of colonies per T25 $cm^2$ flask×100 to the number of cells seeded per T25 $cm^2$.

The behavior of the cells after being placed back in culture and the cloning efficiency were uniform from one biopsy to the other and showed that the cell suspension contained cells capable of proliferating after trypsinization.

Melanocyte Content in the Cell Suspension by Flow Cytometry

The cell membrane was permeabilized in a solution of PBS-1% BSA (bovine serum albumin)-0.5% triton. The primary antibody specific for normal melanocytes (NKI/beteb antibody) was incubated, and then rinsed with PBS-1% BSA. The secondary antibody (Alexa Fluor 488 donkey antimouse antibody) was incubated and then rinsed with PBS-1% BSA. The labeled cells were taken up in PBS and passed through a FACS-SCAN.

The melanocyte/keratinocyte ratios in the epidermal suspensions obtained were comparable to those calculated by Guerra et al. (between 1:30 and 1:200) (Guerra et al., 2003).

In the process described here, the isolated epidermal cells were not placed in culture and the entire process was carried out in one day (biopsy, production of the final product and grafting of noncultured autologous epidermal cells).

Example 3: Use of an Insulating Support for Optimizing the Increasing and the Maintaining of the Temperature of the Medium Using the Warmer 3.1. Materials and Methods Materials and Reagents
  PVC heat packs (warmers), EC labeling.
  Support plates consisting of a polypropylene (PP) sheet 1 to 2 mm thick, folded to obtain a support with a total thickness of 15 mm, having a circular cavity 90 mm in diameter (FIG. 2).
  Compartmentalized Petri dish (ref. Dutscher 020012).
  Temperature probe (thermobouton) programmed to operate with the ThermoTrack V4 and/or A BT 529 software.

Methods

Six milliliters of PBS stored at +4° C., equilibrated at ambient temperature for 20 minutes, are placed in one of the compartments of a Petri dish 90 mm in diameter, in which a thermobouton probe (device for recording temperature variations) is placed in order to take temperature recordings every minute. The Petri dish is then covered with its lid.

The thermobouton probe is in contact with the medium, making it possible to measure temperature variations directly within the solution, after activation of the heat pack. The experiment is carried out by placing or not placing the heat pack and the Petri dish in the circular cavity of the support (FIG. 2). Three different supports were tested. They differ in terms of the more or less central position of the circular cavity intended to receive the warmer and the Petri dish.

Each condition was tested 5 to 6 times, with different temperature probes. The temperature measurements were carried out for 20 min. The mean of the temperatures was calculated over all the values recorded during this period of time.

A statistical analysis of the temperatures measured in the medium with or without support was carried out by means of a student's t test.

3.2. Results

Change in the Temperature of the Medium with a Heat Pack without Support

The temperature data collected by the temperature probe immersed in the medium are represented diagrammatically in FIG. 3. The mean temperature over the 6 tests was 35.5° C., with a mean standard deviation of 3.9° C.

These results demonstrate the reproducibility of the temperatures obtained with the various warmers, without support.

Change in the Temperature of the Medium with a Heat Pack in a Support

Two supports (prototypes V2 and V3) were tested. They differ in terms of the position of the circular cavity intended to receive the warmer. Indeed, in the support V3, this cavity was centralized so as to allow the heat inside the support to be uniform, in order to optimize the increasing and the maintaining of the temperature in the compartmentalized Petri dish placed on the warmer.

The temperature data collected for 20 minutes by the temperature probe immersed in the medium are represented diagrammatically in the graphs presented in FIG. 4 (support V2), in FIG. 5 (support V3) and in FIG. 6 (comparison of the two supports and of the temperatures obtained without support), and summarized in the table below.

TABLE 2

| | Period of time during which temperature maintained >35° C.* | Maximum temperature reached | Time to reach the maximum temperature | Mean temperature of the 6 tests |
|---|---|---|---|---|
| Test without support | 18 min | 39.5° C. | 9 min | 35.5° C. ± 3.9° C. |
| Test with support V2 | 18 min | 40.5° C. | 6 min | 36.7° C. ± 3.6° C. |
| Test with support V3 | 18 min | 40° C. | 9 min | 36.3° C. ± 1° C. |

*period of time obtained over a total time of the experiment of 21 minutes

These results demonstrate:
the reproducibility between the warmers;
the temperatures reached are higher when the warmers are placed in a support (1.1° C. of difference with V2 and 0.8° C. with V3);
with or without support, the medium contained in the compartmentalized Petri dish is maintained at a temperature above 35° C. for at least 18 minutes;
without support, the maximum temperature of 39.5° C. is reached in 9 min, whereas, with the support V2, it reaches 40.5° C. in 6 min.

In order to determine whether the differences observed are statistically significant, a statistical analysis by means of a student's t test was carried out using the values obtained with the support V3. This test indicates a probability of 0.03<0.05, demonstrating that the difference in the temperatures obtained without support and with the support V3 is significant (table 3). The support V3 therefore makes it possible to obtain a temperature which is on average higher than without support, more rapidly and more reproducibly (s.d.±1° C.)

TABLE 3

| | Mean without support | Mean with support |
|---|---|---|
| | 35.4 | 35.9 |
| | 35.9 | 35.7 |
| | 35.7 | 36.9 |

TABLE 3-continued

| | Mean without support | Mean with support |
|---|---|---|
| | 35.3 | 36.3 |
| | 35.3 | 36.8 |
| | 35.6 | NA |
| Mean | 35.5 | 36.32 |
| t | | 0.03 |

The supports therefore make it possible to optimize the increase in temperature and/or the maintaining thereof.

The use of the support of the ViticCell® kit during an enzymatic digestion of a thin skin biopsy in order to produce a dermo-epidermal separation thereof, according to the process for producing epidermal suspensions described in example 2, makes it possible to obtain on average a higher temperature and more rapidly. The support therefore has a double advantage: work plate and optimization of the temperature increase of the heat packs.

REFERENCES

Gauthier, Y. and Surleve-Bazeille, J. E. (1992) Autologous grafting with noncultured melanocytes: a simplified method for treatment of depigmented lesions. *J Am Acad Dermatol*, 26, 191-194.

Guerra, L., Primavera, G., Raskovic, D., Pellegrini, G., Golisano, O., Bondanza, S., Paterna, P., Sonego, G., Gobello, T., Atzori, F., Piazza, P., Luci, A. and De Luca, M. (2003) Erbium:YAG laser and cultured epidermis in the surgical therapy of stable vitiligo. *Arch Dermatol*, 139, 1303-1310.

Mulekar, S. V. (2003) Melanocyte-keratinocyte cell transplantation for stable vitiligo. *Int J Dermatol*, 42, 132-136.

van Geel, N., Ongenae, K., De Mil, M., Haeghen, Y. V., Vervaet, C. and Naeyaert, J. M. (2004) Double-blind placebo-controlled study of autologous transplanted epidermal cell suspensions for repigmenting vitiligo. *Arch Dermatol*, 140, 1203-1208.

The invention claimed is:

1. A process for carrying out an in vitro biochemical reaction for preparing a cell suspension suitable for application to the skin of a patient, the process comprising:
   i) activating a warmer, the operation of which is based on an exothermic physical or chemical process,
   ii) bringing said warmer into contact with a container containing a solution comprising trypsin by placing the warmer and at least the lower part of the container in a cavity of a support,
   iii) placing a skin tissue sample comprising cells suitable for grafting to the skin of the patient in the solution comprising trypsin and incubating at from 30° C. to 40° C. for at least five minutes, and
   iv) isolating cells disassociated from the skin sample and suspending the cells in a solution, to thereby provide a cell suspension suitable for application to the skin of a patient.

2. The process as claimed in claim 1, wherein the contact between the warmer and the container is maintained for at least 10 minutes.

3. The process as claimed in claim 1, wherein the volume of the solution comprising trypsin is from 3 and to 10 ml, the container containing said solution comprising trypsin is a Petri dish having a diameter of from 7 to 11 cm or a compartment of said dish and wherein the warmer is a disk of which the thickness is from 3 to 7 mm and the diameter is from 7 to 11 cm.

4. The process as claimed in claim 1, wherein the cavity of the support is circular, with a diameter from 7 to 11.5 cm, and a depth from 5 to 20 mm.

5. The process as claimed in claim 1, wherein the solution containing trypsin has a concentration of trypsin of from 0.2% to 1%.

6. The process as claimed in claim 1, wherein the cells isolated in iv) are melanocytes.

7. The process as claimed in claim 1, wherein the warmer comprises a hermetic plastic pouch containing a sodium acetate-saturated aqueous solution.

8. The process as claimed in claim 7, wherein the incubating in iii) is at from 30° C. to 37° C. for at least five minutes.

9. The process as claimed in claim 8, wherein the contact between the warmer and the container is maintained for at least 10 minutes.

10. The process as claimed in claim 8, wherein the volume of the solution comprising trypsin is from 3 and to 10 ml, the container containing said solution comprising trypsin is a Petri dish having a diameter of from 7 to 11 cm or a compartment of said dish and wherein the warmer is a disk of which the thickness is from 3 to 7 mm and the diameter is from 7 to 11 cm.

11. The process as claimed in claim 8, wherein the cavity of the support is circular, with a diameter from 7 to 11.5 cm, and a depth from 5 to 20 mm.

12. The process as claimed in claim 8, wherein the solution containing trypsin has a concentration of trypsin of from 0.2% to 1%.

13. The process as claimed in claim 8, wherein the cells isolated in (iv) are melanocytes.

14. The process as claimed in claim 8, wherein the hermetic plastic pouch contains a supercooled sodium acetate-saturated aqueous solution.

\* \* \* \* \*